United States Patent [19]
Yon

[11] Patent Number: 4,829,613
[45] Date of Patent: May 16, 1989

[54] PROTECTIVE PAD FOR POST-OPERATIVE RECOVERY

[75] Inventor: Janet L. Yon, Englewood, Ohio

[73] Assignee: Shumsky Enterprises, Inc., Dayton, Ohio

[21] Appl. No.: 140,474

[22] Filed: Jan. 4, 1988

[51] Int. Cl.⁴ .............................................. A47G 9/00
[52] U.S. Cl. ......................................... 5/431; 5/436; 434/272; D6/601; 128/846
[58] Field of Search ................... 5/431, 434, 436, 441, 5/490, 482; 446/295; D6/596–599, 601; 434/267, 268, 272; 128/132 R

[56] References Cited

U.S. PATENT DOCUMENTS

| | | | |
|---|---|---|---|
| D. 94,702 | 2/1935 | Marks . | |
| D. 109,060 | 3/1938 | Henfield | D6/599 |
| D. 124,296 | 12/1940 | Thompson . | |
| D. 230,804 | 3/1974 | Lijewski | D6/601 |
| D. 256,728 | 9/1980 | Allen | 5/434 |
| 3,109,182 | 11/1963 | Doak | 5/434 |
| 3,148,389 | 9/1964 | Lustig | 5/434 |
| 3,613,133 | 10/1971 | Isola et al. | 5/482 |
| 3,911,512 | 10/1975 | Plate | 5/434 |
| 4,060,863 | 12/1977 | Craig . | |
| 4,091,481 | 5/1978 | Redman | 5/434 |
| 4,173,048 | 11/1979 | Varaney | 5/436 |
| 4,236,263 | 12/1980 | Allee | 5/413 |
| 4,236,264 | 12/1980 | Britzman | 5/441 |
| 4,550,458 | 11/1985 | Fiore | 5/434 |
| 4,683,601 | 8/1987 | Lagin | 5/431 |

FOREIGN PATENT DOCUMENTS 2698 of 1903 United Kingdom ................... 5/490

Primary Examiner—Alexander Grosz
Attorney, Agent, or Firm—Roger S. Dybvig

[57] ABSTRACT

A protective pad for use by a patient during post-operative recovery from open heart surgery comprising a heart-shaped body having a cover made from a substantially dimensionally stable sheet material and a filler comprising a soft stuffing material filling said cover. The front surface of the pad has a diagram of the major coronary arteries which may be marked to indicate areas affected by the surgery.

5 Claims, 2 Drawing Sheets

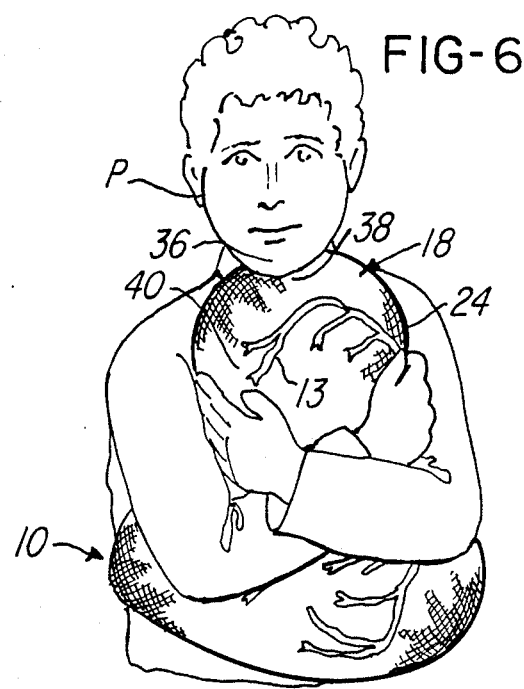

PROTECTIVE PAD FOR POST-OPERATIVE RECOVERY

SUMMARY OF THE INVENTION

This invention relates to protective pads for use by patients recovering from surgery. Although not so limited, this invention relates more particularly to protective pads for use by patients recovering from open heart surgery.

Patients recovering from open heart surgery usually follow a regimen of frequent coughing to expectorate phlegm to clear their lungs. To minimize discomfort, to protect the sternum, and to avoid sternal malunions, the patients use protective pads, typically in the form of conventional pillows, which are held against the patients' chest.

An object of this invention is to provide an improved protective pad for use by a patient recovering from open heart surgery for supporting the sternum when the patient coughs. More particularly, an object of this invention is to provide an improved pad which is easy and comfortable for the patient to use. Another object of this invention is to provide a protective pad that inherently indicates its use and serves as a reminder to the patient or those assisting the patient that the pad is to be used. Another object is to provide a protective pad which provides interest and enjoyment for the patient.

Still another object of this invention is to provide a protective pad which is easy for the patient to hold in proper position for sternum support while providing a chin rest for the patient.

In accordance with this invention, a protective pad comprises a pillow-like, heart-shaped body having a cover formed from a substantially dimensionally stable sheet of fabric or the like material and filled with a soft filler material. The cover and the filler materials are so selected that the pad is reasonably soft yet substantially holds its shape.

The pad is so shaped that it will span all or most of the chest of the average adult patient with the concavity between the two lobes of the heart shape located just below the chin of the patient, so that the patient may rest the chin on the pillow while holding it with the arms. The body tapers to an apex at its bottom end so that the patient can easily and comfortably accommodate to the pad without substantial without discomfort or awkwardness due to interference to movement of the patient's arms by the sides of the pad. A smaller patient may use a smaller pad, or may grip one of the lobes of the pad and hold the pad on its side while resting the chin on the top of the lobe.

To add interest and pleasure to the use of the pad, diagrams of the major coronary arteries are printed on one face of the pad. The diagrams extend from the upper margins of the two lobes, near the bight of the aforementioned concavity, and across both lobes. This provides the patient with a graphic view of the general area of the heart which a doctor or nurse may use to explain the nature of the surgery which has been or soon will be done. Areas of artery blockage or bypass may be marked so that the patient may have a record of the procedures done which can be discussed with family and friends.

Just as one may write upon a cast for a broken bone, one may write messages on the pad of this invention. Thus, the pad of this invention may become a keepsake for recalling the areas affected by the surgery and the messages left by well-wishers. In a preferred embodiment, an ink marker is removably attached to the pad to be available for use by those wanting to write a message on it.

The pad is preferably brightly colored, red being the color of choice since red is conventional for heart-shaped designs suggestive of love or frendship. Its bright color and shape are thought to add a measure of cheer to the patient's recovery room. Furthermore, the shape of the pad as well as the diagram of the arteries are thought to provide a reminder to the patient or one assisting the patient of the need to repeat the coughing procedure. Thus, its very presence in the patient's room is believed to be of benefit to the patient.

Other objects and advantages will become apparent from the following description and the drawings.

BRIEF DESCRIPTION OF THE DRAWINGS

FIG. 6 is a view similar to FIG. 2 illustrating another way in which the pad may be held by a patient.

DETAILED DESCRIPTION

Figure 1:
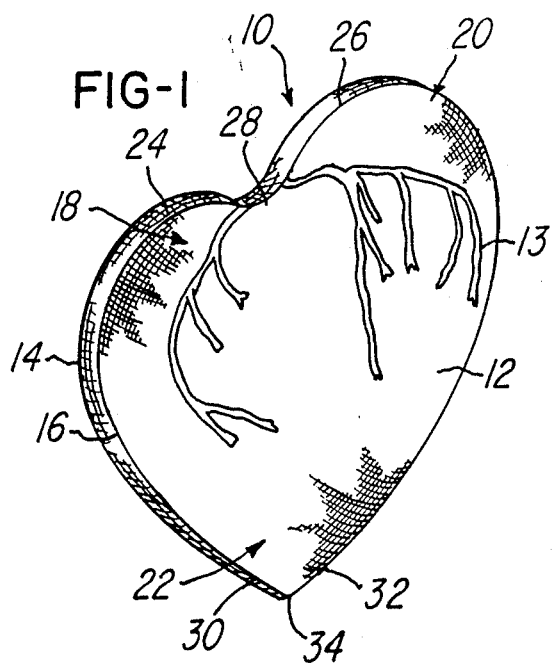
FIG. 1 is a perspective view of a protective pad for post-operative surgery in accordance with this invention, as viewed generally the front of the pad.
Figure 4:
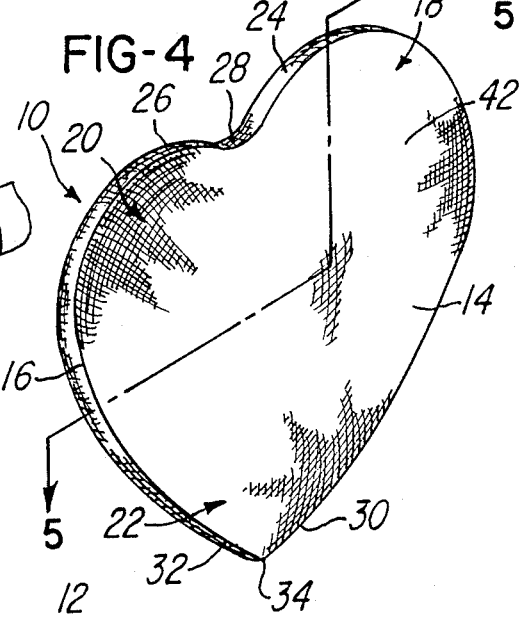
FIG. 4 is a perspective view of the pad of 1, as viewed generally from the rear thereof.

Referring to the drawings in greater detail, a protective pad for post-operative recovery, generally designated 10 is shown in FIGS. 1 and 4 as having a front surface 12 and a rear surface 14 joined together along a marginal edge 16.

In the presently preferred embodiments of the invention, the pad 10 comprises a body which is heart-shaped, that is, in the shape of a Valentine heart, having rounded upper lobes 18 and 20, respectively, and a lower section 22. Lobes 18 and 20 include arcuately convex, outer marginal surfaces 24 and 26, respectively, which connect together to form a centrally located, generally concavely shaped surface region 28. Lower section 22 is generally V-shaped as viewed in either front or rear elevation and includes generally oppositely facing side surfaces 30 and 32 which smoothly converge together to form a lower tip or apex 34.

Figure 2:
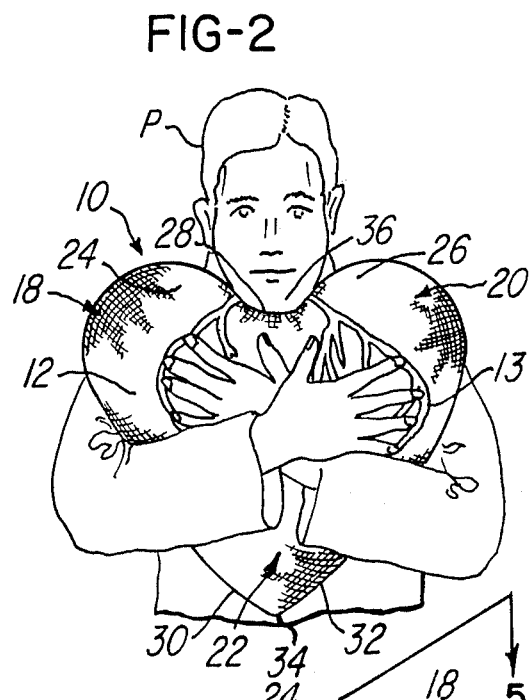
FIG. 2 illustrates the manner in which the protective pad of FIG. 1 may be used by a patient for supporting the sternum when coughing.
Figure 3:
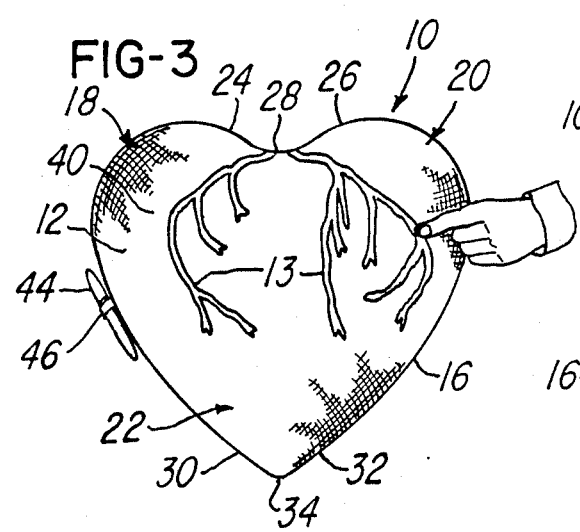
FIG. 3 is a front elevational view of a pad in accordance with this invention, modified from the pad of FIG. 1 by the addition of an ink marker and a holder for removably mounting the marker on the body of the pad, and schematically illustrating the manner in which a protective pad of this invention may be used to explain the surgical procedure to the patient before and after surgery.

FIG. 2 illustrates an adult male patient P preparing to cough by placing the pad 10 against his chest so that his chin 36 rests against the surfaces 24 and 26 of the center concavity 28. The patient P then crosses his arms so that his hands are positioned against the upper, center of the front surface 12, thereby allowing the patient to press the entire back surface 14 against his chest to support the sternum when coughing.

It can be appreciated that the heart-shaped configuration permits the patient generally unrestricted movement of his arms while providing a relatively large sternum support surface 14 and a comfortable surface region 28 for supporting the patient's chin 36. Although the precise size of the pad 10 is not critical, a pad size appropriate for use by adults has a maximum thickness of approxmately 5 inches, a maximum span across the lobes 18 and 20 of approximately 19 inches, a height at its center (from the concavity 28 to the tip 34) of approximately 15 inches, and a length from the top center of each lobe 18 and 20 to the tip 34 of apoproximately 17 inches.

FIG. 6 illustrates how a smaller patient P, in this case a female, may use the pad 10 by grasping one of the lobes, in this case lobe 18, with the pad 10 so oriented that the patient's chin 36 rests on a point, designated 38, along the upper portion of the margin of the arcuate surface 24. The patient P of FIG. 6 then crosses her arms so that her hands are positioned against the front surface portion, designated 40, of the lobe 18 allowing the patient to press only the rear surface, designated 42, of the lobe 18 against her chest. In this way, the protective pad 10 is more easily used by children and smaller adults.

The heart shape of pad 10 is effective to provide a visual aid which can be used by a doctor or nurse to explain a surgical procedure to a patient before and after surgery. The front surface 12 of the pad 10 has printed thereon diagrams 13 of the major coronary arteries by which a doctor or nurse may point out and mark areas of blockage or bypass. This may be done using a marking pen 44 which ma optionally be removably attached to the pad 10 by a fabric band 46 sewn into an outer side edge portion of the pad 10. Pen 46 is also useful for enabling well-wishers to write messages on the pad 10. The diagrams 13 are so located that they are in front of the chest of a patient and visible to others when the patient holds the pad 10 as shown in FIG. 2, with the patient's chin 36 resting on the surfaces 24 and 26. The diagrams 13 extend from the upper margins 24 and 26 of the two lobes 18 and 20, near the concavity 28, and across both lobes 18 and 20.

Referring to FIG. 4, it can be appreciated that the rear surface 14 provides a relatively large surface area which could be used by a doctor or a clinic for printed messages for educational or promotional purposes. For example, a hospital might print a list of its various services available to the patient on the rear surface 14.

Figure 5:
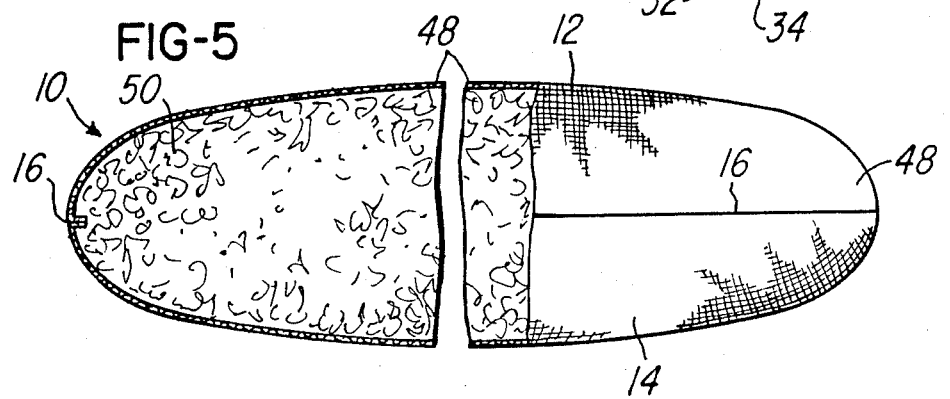
FIG. 5 is a cross-sectional view taken along line 5—5 of FIG. 4.

Referring to FIG. 5, the pad 10 has a cover 48 comprising front and rear sheets 50 and 52, respectively, of a substantially dimensionally stable, markable and printable surface material joined as by sewing along the marginal edge 16. The cover 48 is filled by a soft and resilient stuffing 54. The cover sheets 50 and 52 and the stuffing 54 may be made from various materials. In the presently preferred embodiment, the sheets 50 and 52 comprise a tightly-woven, low-stretch fabric made from a polyester blend having 65 percent Dacron polyester and 35 percent cotton fibers. The preferred stuffing 54 is made with 100 percent polyester fiberfill. The fabric forming the cover sheets 50 and 52 is tightly woven so that the cover 48 will be substantially dimensionally stable. Unless the cover 48 is substantially dimensionally stable, it will be incapable of maintaining the shape of the pad 10, whereupon its appearance, as well as its utility, is substantially diminished. The cover 48 is so formed that, when filled with the stuffing 54, the pad 10 has gently rounded marginal edges for the comfort of the patient.

The pad 10 is preferably a brightly colored red so that it has an overall appearance suggestive of love or friendship. Its shape and color are thought to be cheerful, and along with the printed arteries, serve to remind the patient or one assisting the patient of the need to repeat the coughing procedure.

Although the presently preferred embodiments of this invention have been described, various changes may be made within the scope of the appended claims.

I claim:

1. A protective pad for use by a patient during postoperative recovery from open heart surgery comprising a heart-shaped body having pair of lobes joined by a concave upper marginal surface forming the top center of the heart shape thereof which provides support for the chin of a patient using said pad, a cover made from s substantially dimensionally stable sheet material, and a filler comprising a soft stuffing material filling said cover, said body having a front surface and a rear surface and a diagram of physical features in the area of the human heart on one of said surfaces.

2. The pad of claim 1 wherein said sheet material comprises a tightly woven, low stretch fabric.

3. The pad of claim 2 wherein said sheet material comprises 65 percent Dacron polyester and 35 percent cotton fibers.

4. The pad of claim 2 wherein said diagram extends from said concave upper marginal surface.

5. The pad of claim 1 wherein said diagram comprises a diagram of the major coronary arteries.

* * * * *

UNITED STATES PATENT AND TRADEMARK OFFICE
CERTIFICATE OF CORRECTION

PATENT NO. : 4,829,613
DATED : May 16, 1989
INVENTOR(S) : Janet L. Yon

It is certified that error appears in the above-identified patent and that said Letters Patent is hereby corrected as shown below:

Column 1, line 48, cancel "without" (second occurrence). Column 2, line 23, "generally the" should be --generally from the--; column 2, line 46, "10 is" should be --10, is--. Column 3, line 8, "approxmately" should be --approximately--; column 3, line 12, "apoproximately" should be --approximately--; column 3, line 33, "ma" should be --may--. Column 4, line 33 (claim 1, line 3), "having pair" should be --having a pair--.

Signed and Sealed this

Twenty-first Day of April, 1992

Attest:

HARRY F. MANBECK, JR.

Attesting Officer     Commissioner of Patents and Trademarks